US011524087B2

(12) United States Patent
McCreery et al.

(10) Patent No.: US 11,524,087 B2
(45) Date of Patent: Dec. 13, 2022

(54) MICROWAVE ASSISTED METHODS AND SYSTEMS FOR SURFACE DECONTAMINATION

(71) Applicant: Zeteo Tech, Inc., Sykesville, MD (US)

(72) Inventors: Thomas McCreery, Sykesville, MD (US); Wayne A. Bryden, Sykesville, MD (US)

(73) Assignee: Zeteo Tech, Inc., Sykesville, MD (US)

( * ) Notice: Subject to any disclaimer, the term of this patent is extended or adjusted under 35 U.S.C. 154(b) by 0 days.

(21) Appl. No.: 17/441,289

(22) PCT Filed: Mar. 22, 2020

(86) PCT No.: PCT/US2020/024104
§ 371 (c)(1),
(2) Date: Sep. 21, 2021

(87) PCT Pub. No.: WO2020/198091
PCT Pub. Date: Oct. 1, 2020

(65) Prior Publication Data
US 2022/0096685 A1    Mar. 31, 2022

Related U.S. Application Data

(60) Provisional application No. 62/992,983, filed on Mar. 21, 2020, provisional application No. 62/822,782, filed on Mar. 22, 2019.

(51) Int. Cl.
*A61L 2/12* (2006.01)
*A61L 2/18* (2006.01)

(52) U.S. Cl.
CPC ............... *A61L 2/12* (2013.01); *A61L 2/18* (2013.01); *A61L 2202/14* (2013.01); *A61L 2202/16* (2013.01); *A61L 2202/25* (2013.01)

(58) Field of Classification Search
CPC .......... A61L 2/12; A61L 2/18; A61L 2202/14; A61L 2202/16; A61L 2202/25
See application file for complete search history.

(56) References Cited

U.S. PATENT DOCUMENTS

| 6,039,921 A | 3/2000 | Boucher |
| 6,521,178 B1 | 2/2003 | Goldstein |

(Continued)

FOREIGN PATENT DOCUMENTS

| EP | 3354291 | 8/2018 |
| WO | WO2003015834 | 2/2003 |
| WO | WO2015123194 | 8/2015 |

OTHER PUBLICATIONS

International Preliminary Report on Patentability (IPEA/KR) dated Jun. 30, 2021 for PCT/2020/024104 (with annex).

(Continued)

*Primary Examiner* — Sean E Conley
(74) *Attorney, Agent, or Firm* — Paradice and Li LLP; Anand S. Chellappa

(57) ABSTRACT

Disclosed are microwave assisted methods and systems for decontaminating a variety of contaminated surfaces. The systems and methods comprise treating the surfaces with benign chemical formulations followed by exposing to microwave irradiation for short periods of time to achieve at least 6-log reduction in biological contaminants including spores of *B. anthracis*, *B. thuringiensis*, and *P. roqueforti*. Chemical formulations may comprise copper (II) chloride in water. The formulations may include a surfactant such as a polyethylene sorbitol ester surfactant.

14 Claims, 3 Drawing Sheets

(56) References Cited

U.S. PATENT DOCUMENTS

Figure 1:
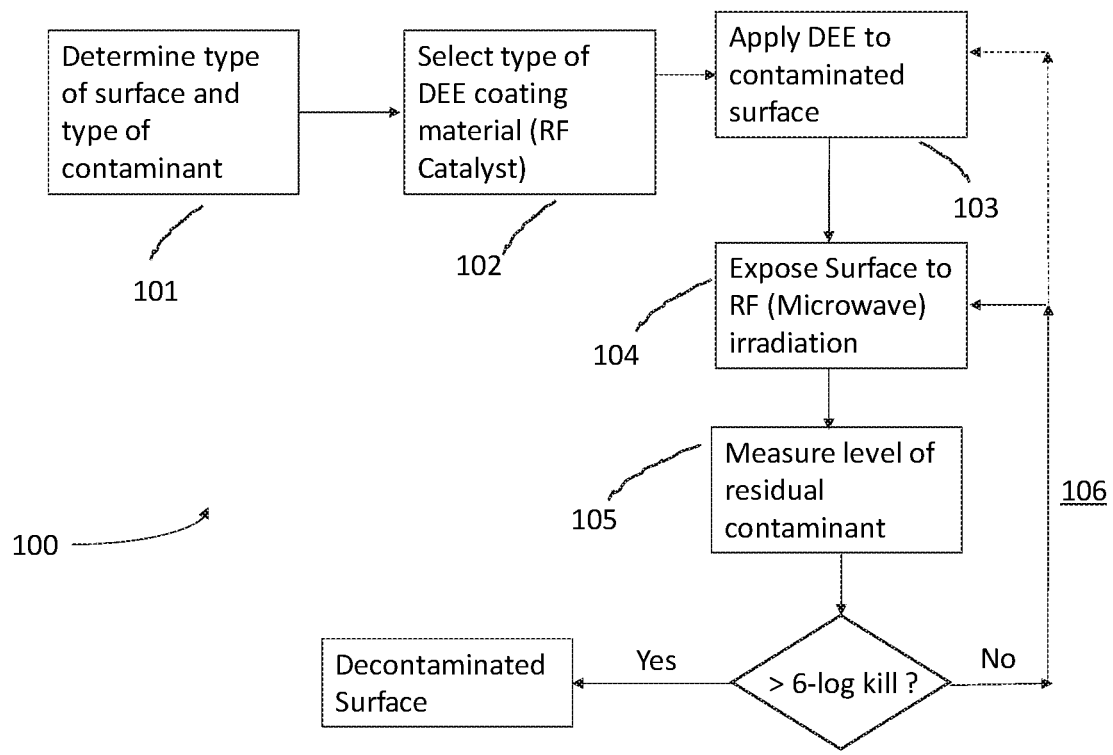

| | | |
|---|---|---|
| 6,797,242 B2 | 9/2004 | Neumann |
| 7,008,592 B2 | 3/2006 | Sias |
| 7,629,918 B2 | 12/2009 | Brown |
| 8,943,744 B2 | 2/2015 | Cohen |
| 2008/0260716 A1* | 10/2008 | Kritzler ............... A61L 2/04 514/579 |
| 2010/0132735 A1 | 6/2010 | Gaus |
| 2014/0205502 A1 | 7/2014 | Park |
| 2017/0368217 A1 | 12/2017 | Berentsveig |
| 2018/0007922 A1 | 1/2018 | Torngren |
| 2018/0154030 A1* | 6/2018 | Erickson ............... A61L 2/12 |

OTHER PUBLICATIONS

Lai, W. et al. "Decontamination of biological warfare agents by a microwave plasma torch," Physics of Plasmas 12, 023501 (2005).
N. van Doremalen, et al. Aerosol and surface stability of HCoV-19 (SARS-CoV-2) compared to SARS-CoV-1. N. Engl. J. Med. 2020; 382:1564-1567.

* cited by examiner

MICROWAVE ASSISTED METHODS AND SYSTEMS FOR SURFACE DECONTAMINATION

RELATED APPLICATIONS

This application is a U.S. National Stage Application of International Application No. PCT/US2020/024104, filed Mar. 22, 2020, which is related to and claims the benefit of U.S. Provisional Application No. 62/822,782, filed Mar. 22, 2019, and entitled "Microwave Assisted Methods and Systems For Surface Decontamination," and U.S. Provisional Application No. 62/992,983, filed Mar. 21, 2020, and entitled "Microwave Assisted Methods and Systems For Surface Decontamination," the entire disclosures of which are incorporated herein by reference in their entireties.

FEDERALLY SPONSORED RESEARCH AND DEVELOPMENT

The disclosure was partly made with U.S. Government support under contract No. HSHQDC-14-C-00050 granted by the U.S. Department of Homeland Security. The U.S. Government may have certain rights in the disclosure.

FIELD

This disclosure relates to methods and systems for decontaminating a variety of contaminated surfaces in both enclosed structures and wide areas. In particular, the systems and methods comprise treating the surfaces with benign chemical formulations followed by exposing to radio frequency irradiation (microwaves) for short periods of time.

BACKGROUND

The threat from aerosolized biological agents remains a key concern of the U.S. Government because of the potentially dire consequences to life and property that may result from such an event. Two prime threat scenarios of particular concern are: (1) release of an agent inside an enclosed structure (e.g., office building, airport, mass transit facility) where HVAC systems could effectively distribute the agents through the entire structure and, (2) wide area release of an agent across an inhabited area such as a town or city. Exposure to the released aerosolized agent could lead to mass casualties. In a wide area release, it is extremely difficult to protect citizens from the initial exposure. Safe, effective and environmentally friendly solutions are needed to mitigate long term effects associated with re-aerosolization and exposure to agents deposited on surfaces and to minimize damage to the surfaces.

Fumigants have been used to decontaminate surfaces exposed to agents released in enclosed structures, such as the Amerithrax attacks that was perpetrated through the mail in 2001. During the U.S. Hart Senate Office Building decontamination, a major challenge was the need to maintain a minimum temperature of 70° F. and minimum relative humidity of 65% RH for the decontaminant, chlorine dioxide (CD), to be stable and effective. At conditions, outside this range, CD decomposes easily to produce chlorine, which is highly reactive and causes damage to surfaces. Further, CD is toxic to humans. A CD concentration of about 700 ppm was used for many hours. The OSHA permissible exposure limit (PEL) for CD is 0.1 ppm, the 15-minute short term exposure limit (STEL) is 0.25 ppm, and the NIOSH immediately damaging to life and health (IDLH) level is 5 ppm. As a result of this clean-up, significant damage to the surfaces in the building was reported.

The use of other fumigants is also problematic. For example, vaporized hydrogen peroxide (VHP) at concentrations of 200 ppm is somewhat less toxic than CD with a PEL of 1 ppm, a STEL of 2 ppm, and an IDLH of 75 ppm. Other examples of fumigants for decontamination are methyl bromide and formaldehyde. Methyl bromide is a well-known, highly potent greenhouse gas and requires the structure to be fully covered to minimize release into the atmosphere. Formaldehyde has only been used in limited applications such as decontaminating small rooms or laboratory instruments. Formaldehyde is a well-known carcinogen, is toxic (PEL of 0.75 ppm, and STEL 2 ppm) and typically leaves a solid polymer residue that must be cleaned from all surfaces to prevent long term outgassing. Fumigants are also not useful for surface decontamination in wide area outdoor release scenarios.

The remediation and restoration industry serves a large and growing market. Total annual expenditures in 2014 for prevention and mitigation of indoor air quality (IAQ) problems in the United States are estimated at approximately $8 billion. A dominant portion of the market is driven by water damage, leading to mold growth. Mold remediation is estimated to be over $3B in market size and is projected to grow rapidly at a rate of approximately 8%. However, only a modest portion of the total market is addressed by chemical or fumigant solutions that have biocidal properties. The total market size for chemical decontamination of mold is estimated to be $150M.

First responders face decontamination or disinfection issues as well. If a wide area dissemination of bio-threat agent occurs, hazmat teams find it challenging to decontaminate their own equipment and vehicles. Decontamination of ambulances that transport patients with infectious diseases such as Ebola Virus Disease or the patients infected by coronavirus types (e.g. COVID-19) is also challenging because ambulances should be remediated prior to being placed back into service. Further, the commercial aviation industry suffered billions in lost revenue during the SARS (severe acute respiratory syndrome) epidemic. The only approved method for decontaminating commercial aircraft involves the wiping down of every single surface in the plane by hand using liquid disinfectants (e.g., diluted bleach) by personnel suited up in protective suits with respirators. It is a painstakingly slow process and is impractical if a large number of aircraft requires decontamination. Other market segments such as the travel and hospitality market have similar needs to treat contamination of cruise ships, buses, trains, and other shared environments. Decontamination of military aircraft using hot and humid air has been tested. Reports indicate that the destruction of spores using high temperature and humidity levels required treatment on the order of 3-4 days. This approach also damages critical systems within the aircraft. Whole building decontamination is expensive and challenging. The Bio-response Operational Testing and Evaluation (BOTE) Project was a multi-agency effort that was designed to test and evaluate, at the scale of a moderately sized building, a response to a *B. anthracis* spore release from initial public health and law enforcement investigation through environmental remediation.

Turning to the healthcare market, cleaning and disinfection functions are done routinely throughout the healthcare industry. Patient rooms, surgery suites, and isolation rooms for highly infectious patients require routine disinfection or in some cases, complete sterilization. The target organisms are typically bacteria, bacterial spores and viruses as opposed to mold. The ventilation systems may also require periodic disinfection.

For decontaminating wide area (outdoor) surfaces, oxidation has been tried to deactivate bio-threat agents on surfaces. Oxidative agents include at least one of hydroxyl radicals that may be produced on-demand at the site, gaseous oxygen, ozone, hydrogen peroxide, hypochlorite (bleach such as sodium hypochlorite and calcium hypochlorite), and chlorine. These chemicals however damage surfaces and are generally toxic to humans. Because of these unfavorable after-effects, the U.S. DOD, for example, has tried biological decontamination of land vehicles using hot soapy water, and of airframe interiors using a combination of hot air and high humidity over long periods of time. These approaches are not effective in destroying biological contaminants.

Decontamination of wide areas surfaces has also been attempted by first exposing the surface to chemicals such as sodium hypochlorite (bleach) and then to microwave radiation to generate highly reactive oxidative species that kill biological agents. For example, 6-log kill (reduction, >99.999% reduction) of *Bacillus anthracis* (Sterne) spores on complex surfaces has been demonstrated by The Raytheon Company and the Los Alamos National Laboratory by spraying the surfaces with dilute household bleach (0.025% sodium hypochlorite) or carbon black followed by activation of the treated surface for a period of about 5 s to 120 s using 95 GHz irradiation. Greater than 6-log reduction in *B. anthracis* was seen at exposure times >5 s. In this hybrid approach, the chemicals used prior to exposing to radio frequency radiation such as microwaves may be viewed as directed energy enhancers ("DEE"). When exposed to RF irradiation, the DEE chemicals generate oxygen containing radicals which has biocidal properties and kills biological contaminants. These reactive species may be continuously generated by treating contaminated surfaces with DEE chemicals and exposing to RF radiation. This hybrid approach has two outstanding advantages over other technologies, namely, (1) it can use extremely low concentrations of decontaminant material which vastly lowers cost and mitigates materials compatibility and environmental contamination problems and, (2) the transient active biocide species (oxygen containing radicals) may be continuously regenerated to prevent the need for reapplication due to interaction with materials. However, bleach is harmful to surfaces. Further, carbon black has the tendency to penetrate into equipment (e.g. computers) found on surfaces and cause electrical short circuits because carbon black is conductive.

U.S. Pat. Pub. No. 20180007922, "METHOD AND SYSTEM FOR MICROWAVE DECONTAMINATION OF FOOD SURFACES," describes a method and a system for decontamination the surface of food items such as meat pieces. The method includes treating the food item and/or the meat piece with microwaves in the range of 0.5-18 GHz, such as 4-18 GHz. The method was used to treat meat pieces that were surface contaminated with *C. botulinum* spores or *C. botulinum* vegetative cells. U.S. Pat. No. 6,797,242, "SYSTEM FOR CHEMICAL AND BIOLOGICAL DECONTAMINATION" discloses a system that produces singlet delta oxygen that neutralizes chemical and biological contaminants. The system can decontaminate large quantities of contaminated air and is not limited by the humidity of the air. U.S. Pat. No. 7,629,918, "MULTIFUNCTIONAL RADIO FREQUENCY DIRECTED ENERGY SYSTEM" discloses a system comprising a radio frequency transmitter and antenna that directs high power electromagnetic energy towards a target sufficient to cause high energy damage or disruption of the target. U.S. Pat. No. 8,943,744, "APPARATUS FOR USING MICROWAVE ENERGY FOR INSECT AND PEST CONTROL AND METHODS THEREOF," discloses an apparatus for using microwave energy for treating a site infested with insects or other small pests. The apparatus comprises a source of microwave energy connected to a power source and a power controller, a transmission element, and an antenna. Methods to use such an apparatus for treatment of an infected site is also disclosed. Lai et al. (2005) disclose a portable microwave plasma torch running with airflow for the decontamination of biological warfare agents. Emission spectroscopy of the plasma torch indicated the production of an abundance of reactive atomic oxygen that could effectively oxidize biological agents. *Bacillus cereus* was chosen as a simulant of *Bacillus anthracis* spores for biological agent in the decontamination experiments. Experimental results showed that all spores were killed in less than 8 s at 3 cm distance, 12 s at 4 cm distance, and 16 s at 5 cm distance away from the nozzle of the torch.

Methods and systems that do not use harmful chemicals are needed to decontaminate surfaces, both in enclosed structures and wide areas, quickly, without any material damage to surfaces or causing side effects in humans, and at low cost. DEE chemical formulations with low chemical toxicity, minimal corrosion, and environmental acceptability are needed. At least 6-log reduction in biological contaminant is desired using low temperature, preferably close to ambient temperature, treatment methods.

BRIEF DISCLOSURE

Disclosed are exemplary methods and systems for decontaminating a variety of surfaces in both enclosed structures and wide areas. In particular, the systems and methods comprise treating the surfaces with benign chemical formulations followed by exposing the surface to radio frequency irradiation (microwave) for short periods of time.

Disclosed is an exemplary microwave assisted surface decontamination method that may comprise the steps of determining at least one of the type of contaminated surface, the type of contaminant on surface, and the concentration of contaminant, selecting a first directed energy enhancer (DEE) formulation, applying the first DEE formulation to the contaminated surface to substantially coat the contaminated surface to form a coated surface, exposing the coated surface to microwave irradiation for a first predetermined time to substantially decontaminate the coated surface to yield a treated surface. The type of surface may comprise at least one of metal, concrete, plastic, and wood. The contaminant may comprise at least one of *B. anthracis, B. thuringiensis, B. globigii*, and *P. roqueforti*. The microwave irradiation may be characterized by a frequency of between about 2.35 GHz and about 2.65 GHz. Alternately, the microwave irradiation may be characterized by a frequency of about 2.45 GHz. Further, the microwave irradiation is characterized by heat output of between about 500 W about 2000 W. The first predetermined time may be between about 10 s and about 120 s. The resulting treated surface may be characterized by a contaminant reduction of at least 6-log reduction.

An exemplary method may further comprise the step of determining the concentration of residual contaminant in at least one of the treated surface and one or more calibrated sample strips and if the contamination reduction is less than 6-log reduction, exposing the treated surface to microwave irradiation for a second predetermined time. The second predetermined time may be the same as or different from that of the first predetermined time. An exemplary method may further comprise the step of determining the concentration of residual contaminant in the treated surface and if the contaminant reduction is less than 6-log reduction, applying a second DEE formulation to the treated surface and exposing the treated surface to microwave irradiation for a second predetermined time. The composition of the second DEE formulation may be the same as or different from that of the first DEE formulation. The DEE formulation may comprise between about 1 wt.-% and about 10 wt.-% percarbonate based stain remover (PCSR), between about 0.05M to about 0.1M copper (II) chloride, and at least about 100 ppm bleach, the balance being water. The concentration of copper (II) chloride may be about 0.06M. The concentration of bleach may be between about 250 ppm and about 1000 ppm. The percarbonate based stain remover may comprise about 66 wt.-% sodium percarbonate and about 34 wt.-% sodium carbonate. Bleach may comprise about 6 wt.-% sodium hypochlorite in water.

Disclosed is an exemplary microwave assisted method to treat a contaminated surface which may comprise the steps of applying a DEE formulation to the contaminated surface to substantially coat the contaminated surface to form a coated surface, and exposing the coated surface to microwave irradiation for a first predetermined time to reduce the concentration of contaminant in the contaminated surface by at least a 6-log reduction. The DEE formulation may comprise between about 1 wt.-% and about 10 wt.-% PCSR, between about 0.05M to about 0.1M copper (II) chloride, and at least about 100 ppm bleach, the balance being water. The concentration of copper (II) chloride may be about 0.06M. The concentration of bleach may be between about 250 ppm and about 1000 ppm. Another DEE formulation may comprise about 1 wt.-% surfactant and about 10 wt.-% PCSR in water. Another DEE formulation may comprise about 1 wt.-% surfactant and about 1 wt.-% PCSR in water. The surfactant may comprise a polyethylene sorbitol ester.

Disclosed is an exemplary system for treating a contaminated surface, which may comprise a tank for storing a directed energy enhancer (DEE) formulation, a plurality of nozzles removably connected to a fluid manifold and in fluid communication with the storage tank for applying the DEE formulation to the contaminated surface to form a coated surface, a microwave generator configured to generate microwaves of predetermined frequency, and a plurality of pyramidal horn antennas for directing the microwaves to the coated surface. The system may further comprise a control system for controlling at least one of the power supply to the microwave generator, the transfer of predetermined dosage of DEE formulation from the tank to the plurality of nozzles, the focusing of the plurality of nozzles to ensure coating of the contaminated surface, the transmission of microwaves from the microwave generator through the plurality of horn antennas, and the focusing of the microwaves on to the coated surface. An exemplary system may be housed in a mobile cart, which may be remotely controllable using the control system. An exemplary system may further comprise data acquisition components and data transfer components for transferring data to a remote server. Data may comprise at least one of the composition of DEE formulation, amount of DEE formulation used for treating a contaminated surface, amount of DEE formulation remaining in the tank, frequency of microwaves, rated power of microwaves, microwave treatment time, and type of contaminant. The cart may be configured to be substantially autonomously operated with minimal human operator input.

Disclosed are exemplary formulations for use in microwave assisted surface decontamination. An exemplary formulation may comprise between about 1 wt.-% and about 10 wt.-% PCSR, between about 0.05M to about 0.1M copper (II) chloride, and at least about 100 ppm bleach, the balance being water. The concentration of bleach may be between about 250 ppm and about 1000 ppm. The concentration of copper (II) chloride maybe about 0.06M.

Disclosed is another exemplary formulation for use in microwave assisted surface decontamination, the formulation comprising about 0.6M copper (II) chloride in water.

Disclosed is another exemplary formulation for use in microwave assisted surface decontamination, the formulation comprising about 0.6M copper (II) chloride and about 0.1M hydrogen peroxide in water.

Disclosed is another exemplary formulation for use in microwave assisted surface contamination, the formulation comprising 0.6M copper (II) chloride, about 0.1M hydrogen peroxide, and about 1 wt.-% polyethylene sorbitol ester surfactant in water.

Disclosed is another exemplary formulation for use in microwave assisted surface contamination, the formulation comprising 0.6M copper (II) chloride, about 0.1M hydrogen peroxide, about 1 wt.-% polyethylene sorbitol ester surfactant, and about 1M sodium chloride in water.

Disclosed is an exemplary system for treating a contaminated surface comprising a tank for storing a directed energy enhancer (DEE) formulation, a plurality of nozzles removably connected to a fluid manifold and in fluid communication with the storage tank for applying the DEE formulation to the contaminated surface to form a coated surface, a fan system to disperse the DEE formulation exiting from the plurality of nozzles, a microwave generator configured to generate microwaves of predetermined frequency, and a plurality of pyramidal horn antennas for directing the microwaves to the coated surface. The system may be housed in a mobile cart. The system may further comprise a control system for controlling at least one of the movement of the cart, the operation of the fan system, power supply to the microwave generator, the transfer of predetermined dosage of DEE formulation from the tank to the plurality of nozzles, the focusing of the plurality of nozzles to ensure coating of the contaminated surface, the transmission of microwaves from the microwave generator through the plurality of horn antennas, and the focusing of the microwaves on to the coated surface. The fan system may be removably disposed on the mobile cart. The fan system may be tethered to the cart wherein the tether provides bidirectional communication with the control system.

Other features and advantages of the present disclosure will be set forth, in part, in the descriptions which follow and the accompanying drawings, wherein the preferred aspects of the present disclosure are described and shown, and in part, will become apparent to those skilled in the art upon examination of the following detailed description taken in conjunction with the accompanying drawings or may be learned by practice of the present disclosure. The advantages of the present disclosure may be realized and attained by means of the instrumentalities and combinations particularly pointed out in the appendant claims.

DRAWINGS

The foregoing aspects and many of the attendant advantages of this disclosure will become more readily appreciated as the same becomes better understood by reference to the following detailed description, when taken in conjunction with the accompanying drawings, wherein:

FIG. 1. Schematic diagram of an exemplary microwave assisted method for surface decontamination.

Figure 2:
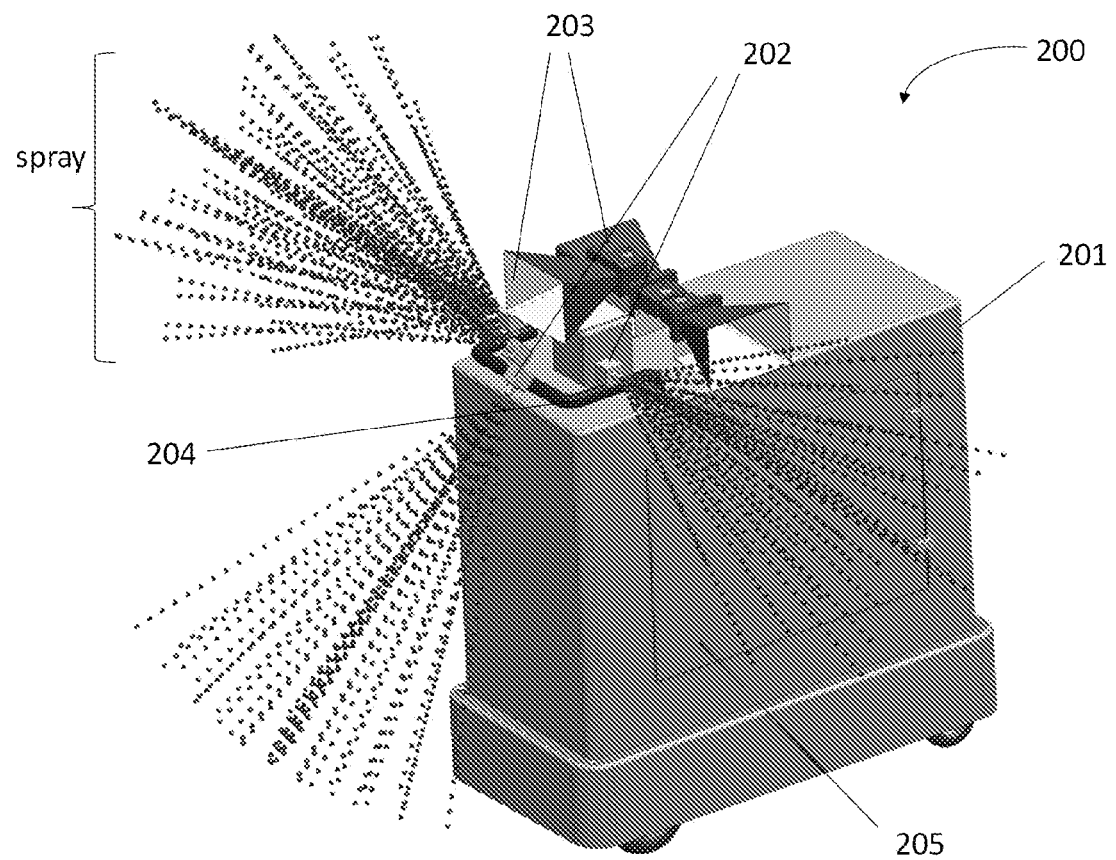

FIG. 2. Perspective view of an exemplary microwave assisted device for surface decontamination.

Figure 3:
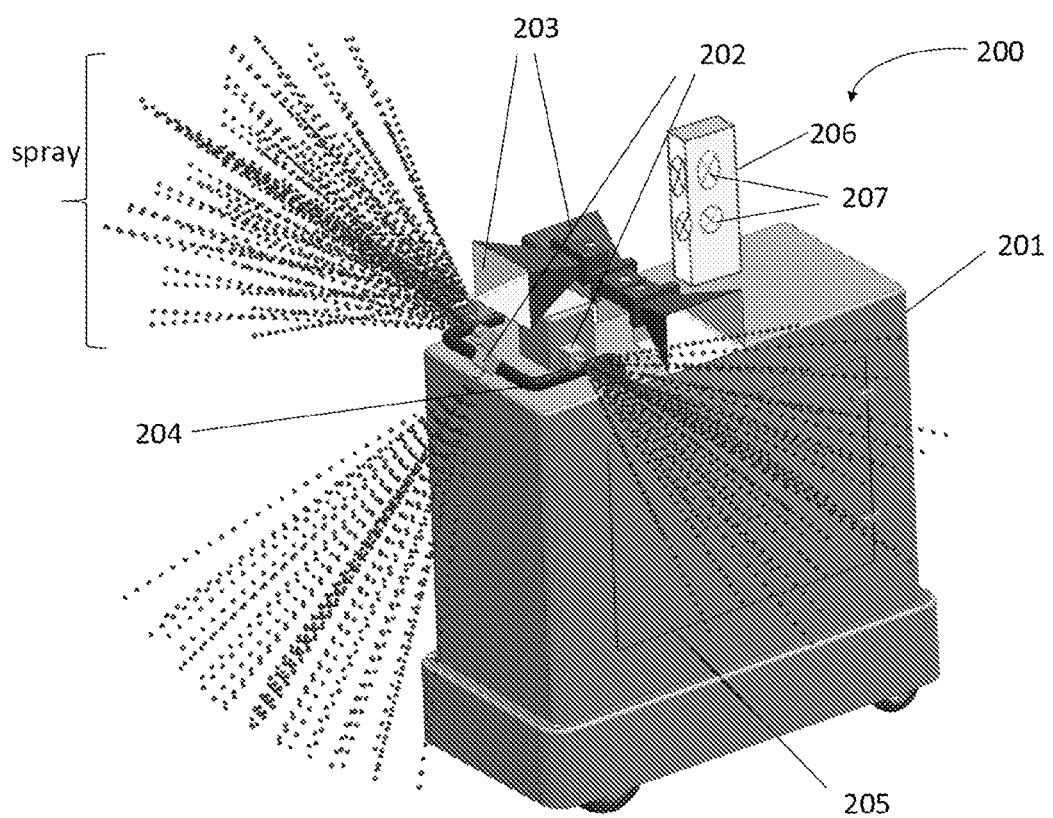

FIG. 3. Perspective view of another exemplary microwave assisted device for surface decontamination.

All reference numerals, designators and callouts in the figures are hereby incorporated by this reference as if fully set forth herein. The failure to number an element in a figure is not intended to waive any rights. Unnumbered references may also be identified by alpha characters in the figures and appendices.

The following detailed description includes references to the accompanying drawings, which form a part of the detailed description. The drawings show, by way of illustration, specific embodiments in which the pilot assembly and methods may be practiced. These embodiments, which are to be understood as "examples" or "options," are described in enough detail to enable those skilled in the art to practice the present invention. The embodiments may be combined, other embodiments may be utilized, or structural or logical changes may be made, without departing from the scope of the invention. The following detailed description is, therefore, not to be taken in a limiting sense and the scope of the invention is defined by the appended claims and their legal equivalents.

In this document, the terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation. Unless otherwise specified in this disclosure, for construing the scope of the term "about," the error bounds associated with the values (dimensions, operating conditions etc.) disclosed is ±10% of the values indicated in this disclosure. The error bounds associated with the values disclosed as percentages is ±1% of the percentages indicated. The word "substantially" used before a specific word includes the meanings "considerable in extent to that which is specified," and "largely but not wholly that which is specified."

DETAILED DISCLOSURE

Particular aspects of the invention are described below in considerable detail for the purpose for illustrating the compositions, and principles, and operations of the disclosed methods and systems. However, various modifications may be made, and the scope of the invention is not limited to the exemplary aspects described.

Exemplary directed energy enhancers ("DEE") are disclosed that generate reactive oxidative species (oxygen radicals that include, but are not limited to, singlet oxygen, OH, OOH radicals and the like) when exposed to radio frequency irradiation. These oxidative species subsequently destroy biological agents that include, but are not limited to, *Bacillus anthracis* (anthrax,) either in spore or vegetative species form and mold (e.g. *Penicillium roqueforti*). Spores are generally resistant to heat, desiccation, chemicals, and radiation. Bacteria can form endospores in approximately 6 to 8 h after being exposed to adverse conditions. The normally-growing cell that forms the endospore is called a vegetative cell. Spores are metabolically inactive and dehydrated.

Exemplary DEE chemical compositions may comprise at least one of copper (II) chloride, ascorbic acid, and a salt in water. The salt concentration may be between about 0.5M and about 1.5M and preferably about 1M. 1M generally refers to 1 mole of solute in 1 liter of solution. The salt may comprise sodium chloride. Copper (II) chloride dihydrate may be used to generate copper (II) ions in solution. The concentration of copper (II) chloride may be between about 0.05M and about 1M, and preferably between about 0.06M and 0.6M. The concentration of ascorbic acid may be about 1M. These chemicals are commonly available food additives, household chemicals, and approved pesticides and fungicides. For example, the copper salt may be a common biocidal/fungicide agent qualified for use with certified organic foods. Ascorbic acid is a chemical component in Vitamin C. Without being bound by any theory, these exemplary compositions are highly effective DEE chemical formulations because they generate reactive oxidative species when exposed to radio frequency (microwave) radiation.

In addition to copper (II) salts, other salts may be used to generate metal ions in solutions. Exemplary metal salts include, but are not limited to, at least one of, or a mixture of casserite (tin oxide), manganite (manganese oxide), transition metal oxides including iron, chromium and cobalt oxides, nickel oxides, zinc oxides, lanthanide oxides, semiconductors such as p-doped and n-doped silicon, gallium arsenide, indium tin oxide, silicon carbide, and refractory metal nitrides and oxides.

Another exemplary DEE chemical composition may comprise about 0.6M copper (II) chloride and about 0.1M ascorbic acid in water. Another exemplary DEE chemical composition may comprise about 0.6M copper (II) chloride, about 0.1M ascorbic acid, and about 1 wt.-% surfactant, the remaining being water. The surfactant ensures good chemical penetration into spore clumps and spreads the chemical over surfaces. An exemplary surfactant may comprise commercially available Tween 80 (Sigma Aldrich) surfactant, which is a polyethylene sorbitol ester that is also known as Polysorbate 80, PEG (80) sorbitan monooleate, and polyoxyethylenesorbitan monooleate. The surfactant may have a calculated molecular weight of 1310 daltons. Typically, the fatty acid composition is approximately 70 wt.-% oleic acid, with the balance being primarily linoleic, palmitic, and stearic acids. The oleic acid concentration is typically >58.0 wt.-%. Another exemplary DEE chemical composition may comprise about 0.6M copper (II) chloride, about 0.1M ascorbic acid, about 1 wt.-% surfactant, and about 1M salt in water.

Another exemplary DEE chemical composition may comprise at least one of a surfactant and percarbonate based stain remover ("PCSR"). An exemplary PCSR is commercially available OxiClean (Church & Dwight Co., Inc.). The PCSR preferably comprises about 66 wt.-% sodium percarbonate (e.g., $2Na_2CO_3:3H_2O_2$) and about 34 wt.-% sodium carbonate. The surfactant concentration in exemplary DEE formulations may be between about 1 wt.-% and 10 wt.-%, and is preferably about 1 wt.-%. The PCSR concentration in exemplary DEE formulations may be between about 1 wt.-% and about 10 wt.-%.

Another exemplary DEE formulation may comprise at least one of copper (II) chloride, surfactant, PCSR, and sodium chloride in water. The sodium chloride concentration in the DEE formulation may be between about 0.5M and about 1.5M, and preferably about 1M. The concentration of copper (II) chloride may be between about 0.05M and about 1M. The surfactant concentration may be between about 0.5 wt.-% and about 1 wt.-%. The surfactant concentration may be about 1 wt.-%. The PCSR concentration may be between about 1 wt.-% and about 10 wt.-%. Another exemplary DEE composition may comprise about 0.06M copper (II) chloride, about 1 wt.-% surfactant, between about 1 wt.-% and about 10 wt.-% PCSR and about 1M salt in water. The salt may comprise sodium chloride.

Another exemplary DEE composition may comprise at least one of a surfactant and bleach in water. An exemplary bleach is Concentrated Clorox Regular Bleach, which comprises about 6 wt.-% sodium hypochlorite (NaOCl). The surfactant concentration may be between about 0.5 wt.-% and about 1 wt.-%. The bleach concentration may be between about 1 wt.-% and 10 wt.-%.

Another exemplary composition may comprise at least one of copper (II) chloride, a surfactant, bleach, and sodium chloride in water. The surfactant concentration may be between about 0.5 wt.-% and about 1 wt.-%. The bleach composition may be between about 1 wt.-% and 10 wt.-%. The sodium chloride composition may be between about 0.5M and about 1M. The copper (II) chloride concentration may be between about 0.05M and 1M. Another exemplary composition may comprise about 0.06M copper (II) chloride, about 1M sodium chloride, about 1 wt.-% surfactant and between about 1 wt.-% and about 10 wt.-% bleach, in water.

Another exemplary composition may comprise at least one of copper (II) chloride, ascorbic acid, and surfactant in water. The surfactant concentration may be between about 0.5 wt.-% and about 1 wt.-%. The ascorbic acid concentration may be between about 0.01M and about 1M. The copper (II) chloride concentration may be between about 0.05M and 1M. Another exemplary DEE composition may comprise about 0.06M copper (II) chloride in water. Another exemplary DEE composition may comprise about 0.06M copper (II) chloride, about 1M sodium chloride, and about 0.1M ascorbic acid.

Another exemplary composition may comprise at least one of copper (II) chloride, hydrogen peroxide, and surfactant in water. The surfactant concentration may be between about 0.5 wt.-% and about 1 wt.-%. The hydrogen peroxide concentration may be between about 0.01M and about 1M. The copper (II) chloride concentration may be between about 0.05M and 1M. Another exemplary composition may comprise about 0.06M copper (II) chloride, about 1M sodium chloride, about 1 wt.-% surfactant, and about 0.1M hydrogen peroxide.

Another exemplary DEE composition may comprise at least one of a surfactant and PCSR in water. The surfactant concentration may be between about 0.5 wt.-% and about 1 wt.-%. The PCSR concentration may be between about 1 wt.-% and about 10 wt.-%. Another exemplary composition may comprise about 1 wt.-% surfactant and about 10 wt.-% PCSR in water. Another exemplary composition may comprise about 1 wt.-% surfactant and about 1 wt.-% PCSR in water.

The microwave radiation may have a frequency of less than about 300 MHz to at least about 300 GHz, such as from about 300 MHz to about 300 GHz, from about 1 GHz to about 125 GHz, or from about 2.4 GHz to about 95 GHz. The frequency may be substantially a single frequency, such as, for example, about 2.4 GHz, about 10 GHz, about 50 GHz, or about 95 GHz. Alternatively, the frequency may vary across a range during an exposure time period, such as from about 1 GHz to about 125 GHz, or from about 2.4 GHz to about 95 GHz. In some embodiments, about 2.45 GHz is used to treat extended surfaces such as the ground or building surfaces. In other embodiments, about 95 GHz is used to treat delicate and/or surfaces with complex shapes.

The Raytheon Company has developed a series of full scale and field deployable 95 GHz systems in support of the Active Denial System (U.S. DOD non-lethal weapons program). These systems may be used for decontaminating surfaces using the exemplary methods disclosed herein. The 95 GHz systems are characterized by output power of 100 W (watts), 400 W, and 100,000 W. The 100 W system is a fixed focus and fixed power output continuous wave system. Power density may be adjusted by varying the distance from the target to the antenna. The 400 W system is variable focus and variable power, pulsed output system and average power may be varied by changing the duty cycle. The 100 kW system is a large-vehicle mounted system with considerable range (in excess of 500 m), and with the ability to change its power output.

FIG. 1 shows a schematic drawing of an exemplary method 100 for microwave assisted surface decontamination using the exemplary DEE formulations disclosed herein. The type of surface and nature of decontaminant may be determined in step 101. The approximate concentration of the contaminant may also be determined in step 101. Exemplary surfaces may comprise at least one of metal, concrete, plastic, and wood. Exemplary contaminants (spore and/or vegetative cells) may comprise at least one of *B. anthracis, B. thuringiensis*, and *P. roqueforti*. Based on the information gathered in step 101, an exemplary DEE formulation as disclosed herein may be selected for surface coating in step 102. In addition to the previously disclosed DEE formulations, another DEE formulation that is effective for decontaminating various types of surfaces may comprise PCSR, copper (II) chloride and bleach in water. The DEE formulation may comprise about 1 wt.-% to about 10 wt.-% PCSR, about 0.05M to about 0.1M copper (II) chloride, and at least about 100 ppm bleach, the balance being water. Another DEE formulation may comprise about 1 wt.-% to about 10 wt.-% PCSR, about 0.06M copper (II) chloride, and at least about 250 ppm bleach, the balance being water. The bleach content is preferably between about 250 ppm and about 1000 ppm. The selected DEE formulation may then be applied to the contaminated surface in step 103 by spraying or other suitable means. Subsequently, the contaminated surface coated with the DEE formulation may be exposed to radio frequency (microwave) irradiation in step 104. The frequency of irradiation is preferably 2.45 GHz that may be generated using commercially available microwave generators. The coated surface may be exposed to irradiation for at least 10 s. The exposure time may be between about 10 s and about 120 s. Alternately, the exposure time may be between about 30 s and about 60 s. At least one of a sample of the treated surface and one or more calibrated test sample strips may be analyzed in step 105 to determine the concentration of the contaminant. The one or more test sample strips may be placed adjacent to the surface being decontaminated. Examples of test sample strips, include but are not limited to, biological indicator spore strips provided by Mesa Labs (Bozeman, Mont.). If at least 6-log reduction in the contaminant is realized, the surface may be deemed to be decontaminated and method 100 may be stopped. If step 105 indicates that additional treatment is required, at least one of steps 103 and 104 may be repeated in step 106. In step 106, the DEE formulation may be modified (e.g., an alternate DEE formulation may be used) to enhance the destruction of surface contaminants. The time period for microwave irradiation exposure may also be increased to achieve at least 6-log reduction of the biological contaminant.

Without being bound by any particular theory, irradiation of the exemplary DEE formulations sprayed on to the contaminated surface may generate at least one of highly reactive singlet oxygen and hydroxyl radicals (including, but not limited to OH, OOH radicals), possibly by the decomposition of hydrogen peroxide released from PCSR in solution, which destroys biological contaminants. Copper (II) chloride may act as a catalyst for peroxide decomposition following a chloride-accelerated copper Fenton type process wherein copper may transition from $Cu^{2+}$ to various oxidation states (redox mechanism) during the decomposition of the peroxide and is continuously regenerated in the process. The decomposition of hydrogen peroxide using transitional metal elements is commonly known as Fenton chemistry. $Cu^{2+}$ may be oxidized to $Cu^{3+}$ during peroxide decomposition upon microwave irradiation and reduced back to $Cu^{2+}$. Alternately, $Cu^{2+}$ may be reduced to $Cu^+$ and re-oxidized to $Cu^{2+}$ following a Cu-Fenton process. Microwave irradiation is believed to accelerate the underlying redox chemistry.

Disclosed is an exemplary decontamination system 200 (FIG. 2) that may be in the form of a mobile cart 201. The system may comprise a container (not shown) for holding a predetermined amount of DEE formulation and fluidic components (e.g., pumps, valves, and the like) to transfer the DEE formulation from the container to manifold 204, which is in fluid communication with one more spraying nozzles 202. The orientation of nozzles 202 may be adjusted to ensure that the contaminated surface may be quickly and completely (or substantially completely) exposed to a spray of DEE formulation. Microwave irradiation (e.g., at about 2.35 GHz to about 2.65 GHz frequency and preferably at about 2.45 GHz frequency) from a microwave generator (not shown) may be directed to the sprayed surface using pyramidal horn antennas 203. The orientation of the antennas may also be adjusted/varied to quickly treat the DEE-sprayed contaminated surface to irradiation. The DEE formulation container and microwave generator may be housed within cart 201 and accessed using door 205. The cart may incorporate a fan system 206 (FIG. 3) comprising one or more fans 207 to disperse the DEE formulation that exits the one or more nozzles 202. One or more fans 207 may be removably installed on the cart for decontamination of small spaces in enclosed structures. Alternately, fan system 206 may be tethered to the cart for decontamination of larger spaces or wide areas. The tether is configured to provide bidirectional communication with the control system (system master controller). The air flow rate output from one or more fans 207 may be scaled in size depending on the size of the space that is to be decontaminated. Preferably, the air flow rating of the one or more fans 207 may be between about 150 cubic feet per minute and about 250 cubic feet per minute and may be varied to optimize DEE formulation dispersion and deposition on contaminated surfaces. In addition to the one or more fans, fan system 206 may comprise power components for operating the fans and control components for communicating with a system master controller. Components such as a power source, magnetron, controllers and microwave transmission elements, and controllers for transfer and spraying of the DEE formulations are preferably housed within cart 201. The master controller may control cart movement, spraying, fan system operation and microwave treatment steps. Commercially available magnetrons such as resonant cavity magnetrons designed for household microwave ovens rated at 500 W to 2 kW may be used. Exemplary system 200 may be used to substantially decontaminate surfaces in enclosed areas (e.g., rooms). The system may be scaled-up to treat surfaces in wide areas (e.g. 1 $km^2$) also. With an exemplary DEE formulation comprising about 1 wt.-% surfactant and about 1 wt.-% PCSR in water, about 2500 kg of DEE (2000 kg of solid PCSR such as OxiClean and 500 kg of Tween 80 surfactant) formulation may be sufficient to decontaminate an area of 1 $km^2$, which represents a 10× reduction in chemical required if a conventional chemical such as Spor-Klenz is used without any microwave irradiation. Spor-Klenz may comprise of about 6% hydrogen peroxide solution or about 0.525% hypochlorite solution (Steris Life Sciences) is used. For an exemplary DEE formulation comprising 0.06M copper (II) chloride in water, 2500 kg of copper (II) chloride may be sufficient to substantially decontaminate surfaces in a 1 $km^2$ area. The exemplary DEE formulations disclosed herein are benign to both surfaces and humans. The DEE formulation sprayer may be in the form of a fogger.

Cart 201 may be configured to be remotely operated by a human operator. The cart may be substantially autonomous; that is, it may be capable of sensing its environment and moving with minimal human input. It may use a plurality of sensors for sensing its surroundings and for navigation, that include, but are not limited to, radar, computer vision, GPS, sonar and gyroscopes.

The exemplary decontamination systems and methods may be used to mitigate insect infestation in the hospitality market in an environmentally friendly manner. Of particular interest is bedbug (*Cimex lectularius*) infestation remediation. Further, the exemplary decontamination systems and methods may be used for hospital room decontamination, defense department equipment decontamination, commercial aircraft decontamination, and first responder/Hazmat equipment decontamination including when the contaminant is a virus such as the COVID-19 coronavirus.

Contaminated surfaces include, but are not limited to concrete, wood, soil, galvanized metal, glass, plastic, and painted wallboard. These surfaces may be treated using the methods disclosed herein to achieve at least 6-log reduction in biological contaminant such as the anthrax simulant *B. thuringiensis*. The decontamination methods may be effective over a wide range of ambient temperature and humidity and in particular, at low temperature/low humidity (about 0° C. to about 25° C. and relative humidity of about 5% to about 40% RH), ambient temperature/medium humidity (about 20° C. to about 30° C. and 40%-50% RH), and high temperature/high humidity conditions (about 30° C. to about 50° C. and relative humidity of about 50% to about 95% RH).

EXAMPLES

Example 1: Destruction of *Bacillus thuringiensis* (BT) Vegetative Cells and Spores Thuricide BT Caterpillar Control (Southern Ag) was used as the source of viable *Bacillus thuringiensis* spores (6 million spores/mg). The DEE chemical comprised of 1:200 bleach in water. This concentration corresponds to approximately 0.5 wt.-% bleach (Clorox) in water. Vegetative cells of BT were grown in lysogeny broth for 48 h at 30° C. The culture was diluted 1:100 with phosphate buffered saline and the DEE chemical composition (about 100 microliters) was added. In the case of spores, the DEE composition was added to achieve a 1:100 dilution of spores.

The spores and vegetative cells in a micro-centrifuge tube were then exposed to 2.45 GHz microwave radiation for 10 s. After exposure, the cells were centrifuged and washed to remove the DEE composition and then plated on Petrifilm and cultured. The plates were then cultured for 24 h at 30° C. This decontamination method resulted in 6-7 log reduction in BT vegetative cells. However, in the case of BT spores, only 4-5 log kill was realized. Increasing the microwave exposure time to 15-20 s yielded 6-7 log kill levels in the case of BT spores.

Example 2: Destruction of Bacillus thuringiensis (BT) Spores Using Bleach-Free Dee Compositions Thuricide BT Caterpillar Control (Southern Ag) was used as the source of viable Bacillus thuringiensis spores (6 million spores/mg). A dilution series was produced from Thuricide BT to show that the material is viable and could be readily cultured on Petrifilm plates. Three DEE chemical compositions were evaluated: (1) about 0.06M copper (II) chloride in water, (2) about 1 wt.-% surfactant and about 10 wt.-% PCSR in water, and (3) about 1 wt.-% surfactant and about 1 wt.-% PCSR in water. OxiClean was used as the PCSR and Tween 80 as the surfactant. During testing of each DEE composition, the DEE composition was added to the spores to yield a 1:100 dilution of spores and exposed to 2.45 GHz microwave radiation for about 10 s. After exposure, the cells were centrifuged and washed to remove the DEE composition and then plated on Petrifilm and cultured for 24 h at 30° C. When using each of the three DEE compositions shown above, the decontamination method destroyed BT spores at 6-7 log kill levels and demonstrated the efficacy of bleach-free treatments.

Example 3: Destruction of Penicillium roqueforti Mold Spores Using Clorox-Free Dee Compositions Penicillium roqueforti spores were suspended in water. Four DEE chemical compositions were evaluated: (1) 0.06M copper (II) ions in water, (2) 1 wt.-% surfactant and 10 wt.-% PCSR, (3) 1 wt.-% surfactant and 1 wt.-% PCSR, and (4) 0.5 wt.-% bleach. OxiClean was used as the PCSR and Tween 80 as the surfactant. Clorox was used as bleach. Each DEE composition was added to 0.1 mg/ml suspension of mold spores and exposed to 2.45 GHz microwave for 10 s. After exposure, the cells were centrifuged, washed to remove the DEE chemicals and then plated on Petrifilm and cultured. With the DEE composition 0.06M copper (II) ions in water and 1 wt.-% surfactant and 10 wt.-% sodium percarbonate, a 6-7 log reduction in P. roqueforti spores (6-7 log kill levels) was realized.

Example 4: Decontamination of Glass and Plastic Surfaces Exposed to BT and Penicillium roqueforti Mold Spores Using Clorox-Free Dee Compositions Untreated microscope slides were chosen as the glass coupons. Plastic plant labels were chosen as the plastic coupons. These surfaces were coated with 500 microliters of a 1:100 dilution of Thuricide (BT) or Penicillium roqueforti spores and DEE formulation and dried. To eliminate any vegetative cells, spore recovery involved hydration with 1-10 mL (depending on coupon size) of aqueous 0.1 M PBS (phosphate buffered saline, sterile) followed by sonication for 15 minutes and heat shock at 70° C. for 2 hours to remove vegetative cells. DEE formulations were then applied to the spore area. The coupons (glass and plastic) were then exposed to 2.45 GHz radio frequency radiation for 10 s to 30 s and then washed. The spores were centrifuged and washed to remove the DEE chemicals. The washed spores were then plated on Petrifilm. Dilutions for plating were at 100 microliters total plating volumes on Petrifilm. The volume of PBS was changed on the coupon in order to saturate for high recovery. When testing included DEE compositions with copper (II) chloride, PBS was exchanged with deionized water to avoid precipitation of copper by PBS.

Three DEE chemical compositions were evaluated: (1) about 0.06M copper (II) chloride in water, (2) about 1 wt.-% surfactant and about 10 wt.-% PCSR in water, and (3) about 1 wt.-% surfactant and about 1 wt.-% PCSR in water. With all three compositions, >6-log kill was observed for BT on plastic and glass coupons.

In the case of P. roqueforti mold spores, treatment with DEE chemical compositions (2) and (3) above followed by RF treatment at 30 s resulted in >6-log kill on glass coupons. In the case of plastic coupon treatment, only composition (2) above resulted in >6-log kill.

Example 5: Destruction of BT Spores Using Clorox-Free Dee Compositions and Exposure to 95 GHz RF (Microwave) Radiation 1:100 dilution of BT spores in DEE chemical formulations were prepared in a 96-well microtiter plate. Three DEE chemical compositions were evaluated: (1) about 0.06M copper (II) chloride in water, (2) about 1 wt.-% surfactant and 10 wt.-% PCSR in water, and (3) about 1 wt.-% surfactant and about 1 wt.-% PCSR in water. The top of the wells was sealed with a polyolefin sheet. The plates were oriented vertically and were then exposed to 95 GHz RF radiation (centered at 94 GHz) for about 30 s to about 60 s. After RF exposure, the spores were centrifuged, washed to removed DEE chemicals, plated on Petrifilm and cultured. With formulation (2), >6-log kill was realized at both 30 s and 60 s.

Example 6: Destruction of Bacillus globigii Using Exemplary Dee Formulations and Exposure to 2.5 GHz RF (Microwave) Radiation Table 1 lists exemplary DEE formulations that were effective in achieving >6-log reduction of B. globigii (BG) after 30 s of 2.45 GHz irradiation. OxiClean was used as the PCSR and Tween 80 as the surfactant. Clorox was used as bleach. The pH of these formulations is also shown in Table 1. As can be seen, the pH of these formulations ranges from about 1.84 to about 10.33 with an error range of ±0.1. BG is a Gram-positive, spore-forming bacteria and is commonly found in dust, soil and water. BG may be used to simulate biological warfare agents. BG is also a well-known cause of food poisoning, resulting in diarrhea and vomiting.

TABLE 1

Exemplary DEE formulations and pH.

| Label | DEE formulation | pH |
|---|---|---|
| A | 0.6M $CuCl_2$ | 3.25 |
| B | 0.6M $CuCl_2$, 0.1M $H_2O_2$ | 3.3 |
| C | 0.6M $CuCl_2$, 0.1M $H_2O_2$, 1 wt.-% surfactant | 3.03 |
| D | 0.6M $CuCl_2$, 0.1M $H_2O_2$, 1 wt.-% surfactant, 1M NaCl | 3.11 |
| O | 0.06M $CuCl_2$, 0.1M ascorbic acid, 1 wt.-% surfactant | 1.84 |

TABLE 1-continued

Exemplary DEE formulations and pH.

| Label | DEE formulation | pH |
|---|---|---|
| S | 0.06M $CuCl_2$, 10 wt.-% PCSR, 1 wt.-% surfactant, 1M NaCl | 10.33 |
| X | 0.06M $CuCl_2$, 1 wt.-% bleach, 1 wt.-% surfactant, 1M NaCl | 4.33 |

Formulations A, B, C, D with pH between about 3.03 and about 3.25 were more effective than the other formulations listed in Table 1. Further, bleach compositions in concentrations of between about 0.25 wt.-% and about 0.5 wt.-% in water were effective in achieving >6-log reduction of BG after 30 s of 2.45 GHz irradiation. The pH of these compositions was measured to be about 9.01 (0.25 wt.-% bleach) and about 9.65 (0.5 wt.-% bleach), with an error range of ±0.1 associated with these pH measurements.

The Abstract is provided to comply with 37 C.F.R. § 1.72(b), to allow the reader to determine quickly from a cursory inspection the nature and gist of the technical disclosure. It should not be used to interpret or limit the scope or meaning of the claims.

Although the present disclosure has been described in connection with the preferred form of practicing it, those of ordinary skill in the art will understand that many modifications can be made thereto without departing from the spirit of the present disclosure. Accordingly, it is not intended that the scope of the disclosure in any way be limited by the above description.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this disclosure is entitled. It should be understood that all actions may be expressed as a means for taking that action or as an element which causes that action. Similarly, each physical element disclosed should be understood to encompass a disclosure of the action which that physical element facilitates.

In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Further, the use of the transitional phrase "comprising" is used to maintain the "open-end" claims herein, according to traditional claim interpretation. Thus, unless the context requires otherwise, it should be understood that variations such as "comprises" or "comprising," are intended to imply the inclusion of a stated element or step or group of elements or steps, but not the exclusion of any other element or step or group of elements or steps. Such terms should be interpreted in their most expansive forms so as to afford the applicant the broadest coverage legally permissible.

REFERENCES

1. Lai W. et al. "Decontamination of biological warfare agents by a microwave plasma torch," Physics of Plasmas 12, 023501 (2005).

What is claimed is:

1. A microwave assisted surface decontamination method, the method comprising:

determining at least one of the type of contaminated surface, the type of contaminant on surface, and the concentration of contaminant wherein the contaminated surface is at least one of a surface disposed inside an enclosed structure and a surface disposed in an outdoor wide area;

selecting a first directed energy enhancer (DEE) formulation;

spraying the first DEE formulation to the contaminated surface to substantially coat the contaminated surface to form a coated surface; and, exposing the coated surface to microwave irradiation for a first predetermined time to substantially decontaminate the coated surface to yield a treated surface wherein the treated surface is characterized by a contaminant reduction of at least 6-log reduction and wherein the spraying the first DEE formulation step and exposing the coated surface to microwave irradiation step are performed using a decontamination system comprising:

a tank for storing the DEE formulation;

a plurality of nozzles removably connected to a fluid manifold and in fluid communication with the storage tank for spraying the DEE formulation to the contaminated surface to substantially coat the contaminated surface to form a coated surface;

a microwave generator configured to generate microwaves of predetermined frequency; and, a plurality of pyramidal horn antennas for directing the microwaves to the coated surface.

2. The method of claim 1 wherein the type of surface comprises at least one of metal, concrete, plastic, and wood.

3. The method of claim 1 wherein the contaminant comprises at least one of *B. anthracis, B. thuringiensis, B. globigii*, and *P. roqueforti*.

4. The method of claim 1 wherein the microwave irradiation is characterized by a frequency of between about 2.35 GHz and about 2.65 GHz.

5. The method of claim 1 wherein the microwave irradiation is characterized by a frequency of about 2.45 GHz.

6. The method of claim 1 wherein the microwave irradiation is characterized by heat output of between about 500 W about 2000 W.

7. The method of claim 1 wherein the first predetermined time is between about 10 s and about 120 s.

8. The method of claim 1 further comprising the step of determining the concentration of residual contaminant in at least one of the treated surface and one or more calibrated sample strips and if the contamination reduction is less than 6-log reduction exposing the treated surface to microwave irradiation for a second predetermined time following directly after the microwave irradiation step for the first predetermined time.

9. The method of claim 8 wherein the second predetermined time is different from that of the first predetermined time.

10. The method of claim 8 wherein the second predetermined time is the same as that of the first predetermined time.

11. The method of claim 1 further comprising the step of determining the concentration of residual contaminant in the treated surface and if the contaminant reduction is less than 6-log reduction applying a second DEE formulation to the treated surface and exposing the treated surface to microwave irradiation for a second predetermined time.

12. A microwave assisted method to treat a contaminated surface, the method comprising:
   spraying a DEE formulation to the contaminated surface to substantially coat the contaminated surface to form a coated surface; and,
   exposing the coated surface to microwave irradiation for a first predetermined time to reduce the concentration of contaminant in the contaminated surface by at least a 6-log reduction wherein the DEE formulation comprises between about 1 wt.-% and about 10 wt.-% PCSR, between about 0.05M to about 0.1M copper (II) chloride, and at least about 100 ppm bleach, the balance being water.

13. A microwave assisted method to treat a contaminated surface, the method comprising:
   spraying a DEE formulation to the contaminated surface to substantially coat the contaminated surface to form a coated surface wherein the contaminated surface is at least one of a surface disposed inside an enclosed structure and a surface disposed in an outdoor wide area; and,
   exposing the coated surface to microwave irradiation for a first predetermined time to reduce the concentration of contaminant in the contaminated surface by at least a 6-log reduction and wherein the spraying the DEE formulation step and exposing the coated surface to microwave irradiation step are performed using a decontamination system comprising:
   a tank for storing the DEE formulation;
   a plurality of nozzles removably connected to a fluid manifold and in fluid communication with the storage tank for spraying the DEE formulation to the contaminated surface to substantially coat the contaminated surface to form a coated surface;
   a microwave generator configured to generate microwaves of predetermined frequency; and,
   a plurality of pyramidal horn antennas for directing the microwaves to the coated surface.

14. A microwave assisted method to treat a contaminated surface, the method comprising:
   spraying a DEE formulation to the contaminated surface to substantially coat the contaminated surface to form a coated surface using a decontamination system wherein the contaminated surface is disposed outside the system; and,
   exposing the coated surface to microwave irradiation for a first predetermined time using the decontamination system wherein the contaminated surface is disposed outside the system to reduce the concentration of contaminant in the contaminated surface by at least a 6-log reduction and wherein the contaminated surface is at least one of a surface inside a building, inside an aircraft, inside an ambulance, and a surface disposed in an outdoor wide area.

* * * * *